(12) United States Patent
Crawford et al.

(10) Patent No.: US 7,099,012 B1
(45) Date of Patent: Aug. 29, 2006

(54) IN-LINE SPECTROMETER

(75) Inventors: James Crawford, Sunnyvale, CA (US); David Doting, Morgan Hill, CA (US); Robert Ellison, San Francisco, CA (US); Sang Hoang, Campbell, CA (US); Steven Monsef, Los Gatos, CA (US); Frank J. Szczurko, Jr., Menlo Park, CA (US)

(73) Assignee: Turner Designs, Inc., Sunnyvale, CA (US)

( * ) Notice: Subject to any disclaimer, the term of this patent is extended or adjusted under 35 U.S.C. 154(b) by 89 days.

(21) Appl. No.: 10/687,520

(22) Filed: Oct. 15, 2003

Related U.S. Application Data

(60) Provisional application No. 60/454,588, filed on Mar. 13, 2003.

(51) Int. Cl.
*G01N 21/64* (2006.01)
*G01N 21/53* (2006.01)

(52) U.S. Cl. ............ 356/417; 356/416; 356/441; 250/458.1

(58) Field of Classification Search ........... 356/417, 356/317, 318, 436, 437, 432; 250/458.1, 250/459.1, 461.1–461.2, 573, 574, 576
See application file for complete search history.

(56) References Cited

U.S. PATENT DOCUMENTS

| | | | | |
|---|---|---|---|---|
| 3,665,201 A | * | 5/1972 | Shea et al. | 250/574 |
| 4,072,424 A | * | 2/1978 | McMullan et al. | 356/442 |
| 4,293,225 A | * | 10/1981 | Wheaton et al. | 356/417 |
| 4,553,034 A | * | 11/1985 | Byers et al. | 250/458.1 |
| 5,013,150 A | * | 5/1991 | Watts et al. | 356/73 |
| 5,331,177 A | * | 7/1994 | Kubisiak et al. | 250/574 |
| 5,350,922 A | * | 9/1994 | Bartz | 250/574 |
| 6,255,118 B1 | * | 7/2001 | Alfano et al. | 436/172 |
| 6,307,630 B1 | * | 10/2001 | Banerjee | 356/436 |
| 6,369,894 B1 | * | 4/2002 | Rasimas et al. | 356/417 |
| 6,836,325 B1 | * | 12/2004 | Maczura et al. | 356/328 |

OTHER PUBLICATIONS

Skoog, D.A._Principles of Instrumental Analysis, 3rd Ed._Saunders College Publishing, 1985, p. 19.*

* cited by examiner

*Primary Examiner*—F. L. Evans
(74) *Attorney, Agent, or Firm*—Stattler, Johansen & Adeli LLP

(57) ABSTRACT

Some embodiments of the invention provide an improved spectrometer that measures light emissions and/or reflection from a non-solid material that flows through a system of pipes. This spectrometer is designed to fit into a standard pipe system. The material flows past a distal end of the spectrometer that is inserted in the pipe system. The spectrometer has the ability to project light onto the material and collect a resulting light from the material through the distal end as the material flows past this end.

36 Claims, 11 Drawing Sheets

IN-LINE SPECTROMETER

CLAIM OF BENEFIT TO PRIOR PROVISIONAL APPLICATION

This application claims benefit to U.S. Provisional Patent Application 60/454,588, filed on Mar. 13, 2003, which is incorporated herein by reference.

BACKGROUND

Fluorescence occurs when a substance receiving a light of a certain color (excitation) emits a light of a different color (emission). The wavelength of the emission is typically longer than that of the excitation. A fluorometer is a device that measures fluorescence by supplying an excitation source, detecting the resulting emission, and converting the emission into an electrical signal proportional to fluorescence. This electrical signal can be used to drive a display to show the fluorescent signal and/or used as a control signal for controlling processes. There are various implementations of fluorometers. A spectrofluorometer allows the user to select the excitation and/or emission wavelengths. A scanning spectrofluorometer can scan the excitation and/or emission over a range of wavelengths.

Fixed filter fluorometers are used when low cost and/or reliability are desirable. Fixed filter fluorometers have a light source with an optional filter to select an optimal excitation wavelength. The detector also has a filter to select the optimal emission wavelength, which is different from the excitation wavelength. Typically, the excitation source and the emission detector are positioned at a 90° angle from each other, though this may change depending on the application.

Fluorometers are used in a wide variety of applications, including but not limited to environmental studies, leak detection, dye tracer studies, and industrial control. In industrial control applications, an inert fluorescent tracer is bonded with a control chemical of interest (for example, a biocide to prevent biological growth within a cooling system). The quantity of the fluorescent tracer is directly proportional to the control chemical. As the control chemical is consumed the amount of fluorescent tracer will drop. Using a fluorometer to detect the amount of fluorescent tracer allows the user to indirectly measure the control chemical. Using this fluorescent measurement the user can accurately control the amount of control chemical in the system. This can be as simple as turning on a pump when the fluorescent signal drops to a certain level (thus adding the control chemical to the system) and turning off the pump when the fluorescent signal reaches a desired level. More complex algorithms can be used as well.

A limitation of current fixed filter fluorometers for industrial control is that they must be supplied a water stream from the system of interest. Additional plumbing must be installed, usually with safety features, to supply water to the fluorometer and to either return the water to the system or dispose of it. This additional plumbing adds cost, labor, and complexity to the system. These fluorometers usually have a flow cell, which is a clear tube through which the sample water flows so that the fluorescence can be detected. This flow cell can become fouled (become less optically clear) which reduces the fluorescent signal. If the flow cell remains fouled then an error is introduced into the control of the system. Since this is undesirable, a periodic maintenance is usually required to clean the flow cell, again adding undesirable labor and cost. An example of such a fluorometer is described in U.S. Pat. No. 6,369,894.

Therefore, there exists a need for a fluorometer that can be introduced directly into a stream of non-solid material. This greatly reduces the installation requirements for the fluorometer and eliminates the flow cell, thus reducing maintenance requirements. More generally, there is a need for a spectrometer that can easily be introduced into a stream of a non-solid material.

SUMMARY

Some embodiments of the invention provide an improved spectrometer that measures light emission and/or reflection from a non-solid material that flows through a system of pipes. This spectrometer is designed to fit into a standard pipe system. The material flows past a distal end of the spectrometer that is inserted in the pipe system. The spectrometer has the ability to project light onto the material and collect a resulting light from the material through the distal end as the material flows past this end.

DESCRIPTION OF THE DRAWINGS

The novel features of the invention are set forth in the appended claims. However, for purposed of the explanation, several embodiments of the invention are set forth in the following figures.

DETAILED DESCRIPTION

In the following description, numerous details are set forth for purpose of explanation. However, one of ordinary skill in the art will realize that the invention may be practiced without the use of these specific details. In other instances, well-known structures and devices are shown in block diagram form in order not to obscure the description of the invention with unnecessary detail.

Figure 1:
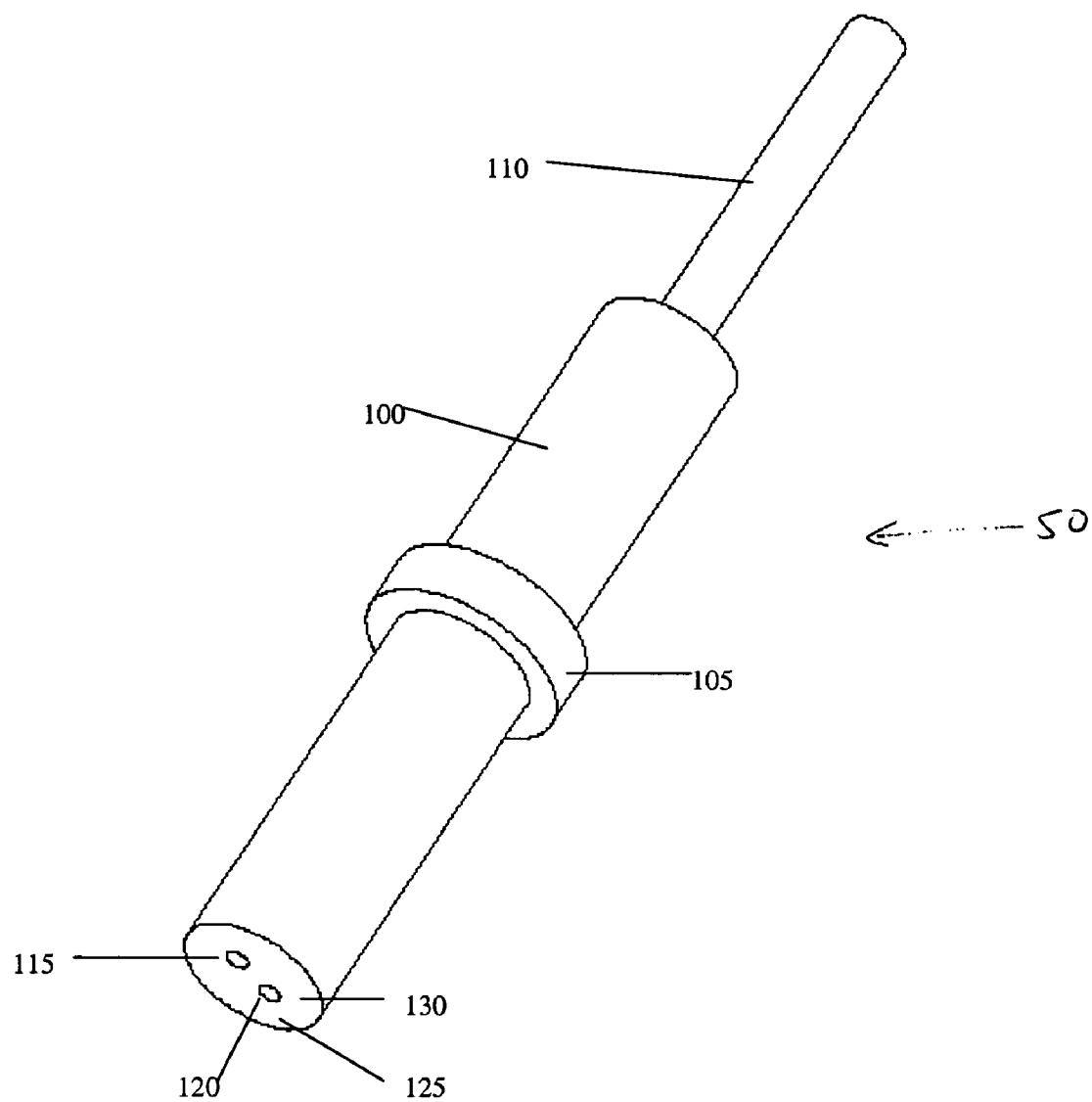
FIG. 1 is an outside view of the fluorometer.
Figure 2:
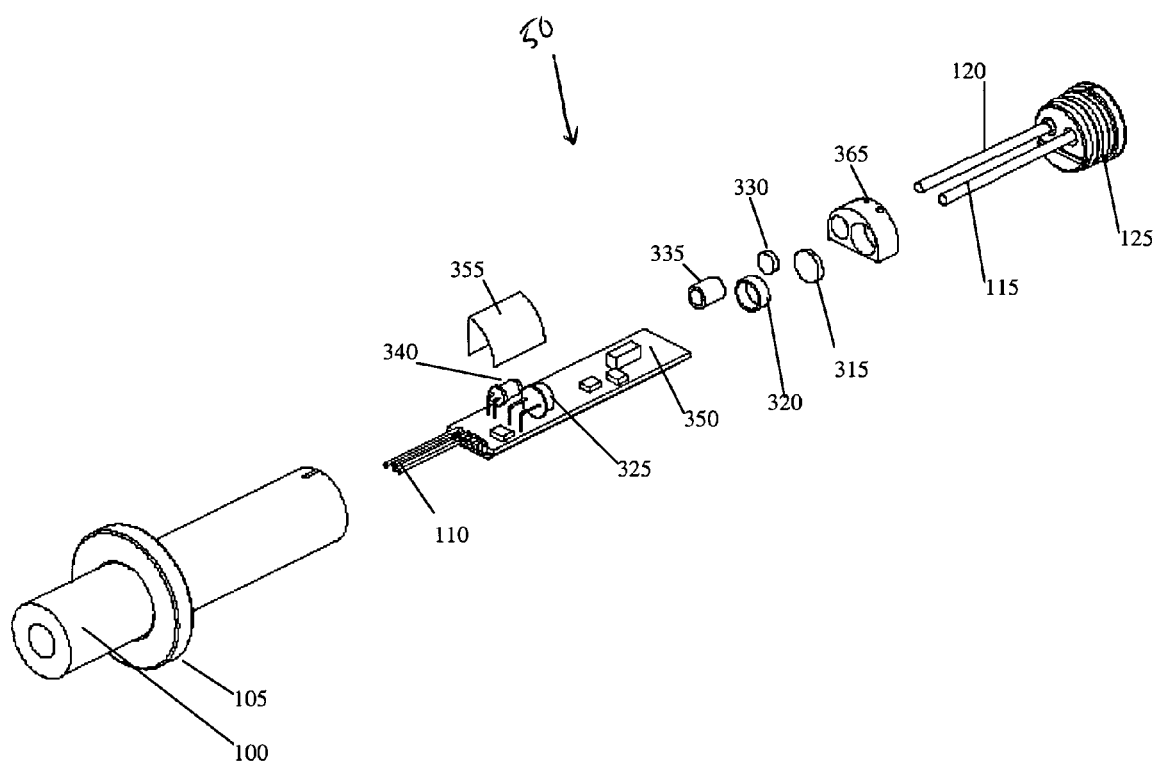
FIG. 2 is an exploded view of the preferred embodiment of the fluorometer.
Figure 3:
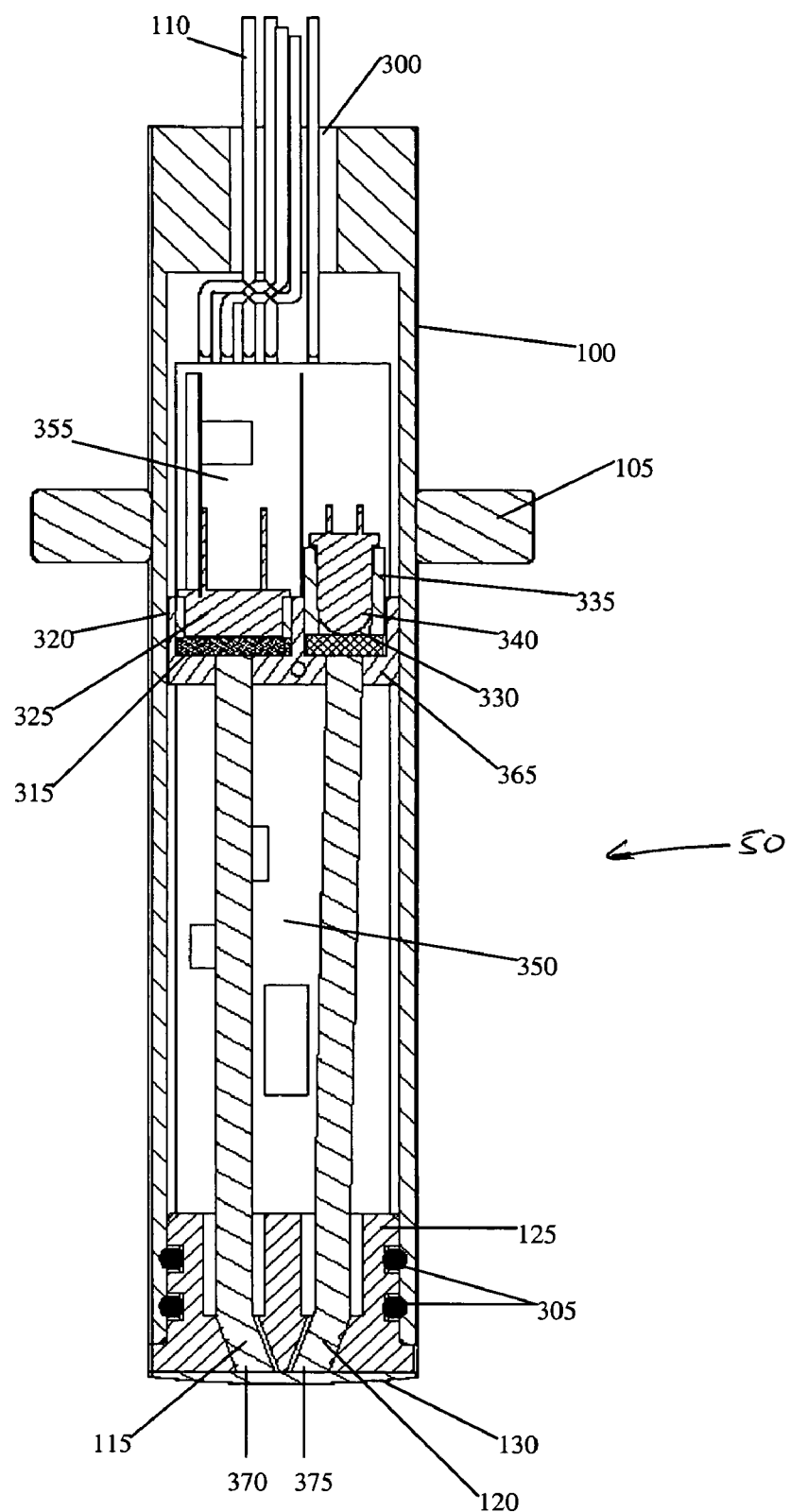
FIG. 3 is a cross-sectional view of the preferred embodiment of the fluorometer.

FIGS. 1–3 illustrate a fluorometer 50 of some embodiments of the invention. FIG. 1 illustrates a perspective view of the outside of the fluorometer 50 as seen by the user, FIG. 2 illustrates an exploded view of the fluorometer 50, and FIG. 3 illustrates a cross-sectional view of the fluorometer 50. This fluorometer is designed to fit into a standard pipe system and measure the fluorescence of a non-solid material (e.g., a liquid, vapor, etc.) flowing through this system. The material flowing through the pipe system is water in the examples described below. However, one of ordinary skill will realize that the invention's fluorometers can be used to gauge the fluorescence of any non-solid material (e.g., any liquid or vapor). Also, even though several fluorometers are described below, several aspects of the invention are applicable to other types of spectrometers, such as turbidimeters.

As shown in these figures, the fluorometer 50 includes a tube housing 100, a collar 105, an electrical cable 110, two fiber optic cables 115 and 120, a cap 125, an optical coating 130, o-rings 305, an emission filter 315, sleeves 320 and 335, a photodiode 325, an excitation filter 330, a light emitting diode (LED) 340, a printed circuit board (PCB) 350, a metal shield 355, and an optical chassis 365.

The tube housing 100 houses several components of the fluorometer, such as fiber optic cables 115 and 120 and the PCB 350, which houses the electronic circuitry of the fluorometer. This housing is made of a water resistant material, such as PVC or delrin, although other plastics or metals could be used depending on the possible chemical interactions between the material and the process water. Collar 105 is provided to set the height of the tube housing, and thereby set the proper height of the fluorometer in the process water. This collar also provides a sealing surface when the fluorometer is mounted in an installation tee fitting, as further described below.

Cable 110 is a cable connection that includes several conductors (e.g., several wires). Power is supplied to the fluorometer through cable 110. Optional control lines that can change the sensitivity and dynamic range of the fluorometer can also be supplied to the fluorometer 50 through cable 110. Cable 110 also provides a signal out that is proportional to fluorescence. This signal can be either (1) an analog signal (for example, 0 to 5 volts or 4 to 20 ma) that can be detected by typical industrial controllers, or (2) a digital output that can be read by computers or computer based controllers.

Figure 4:
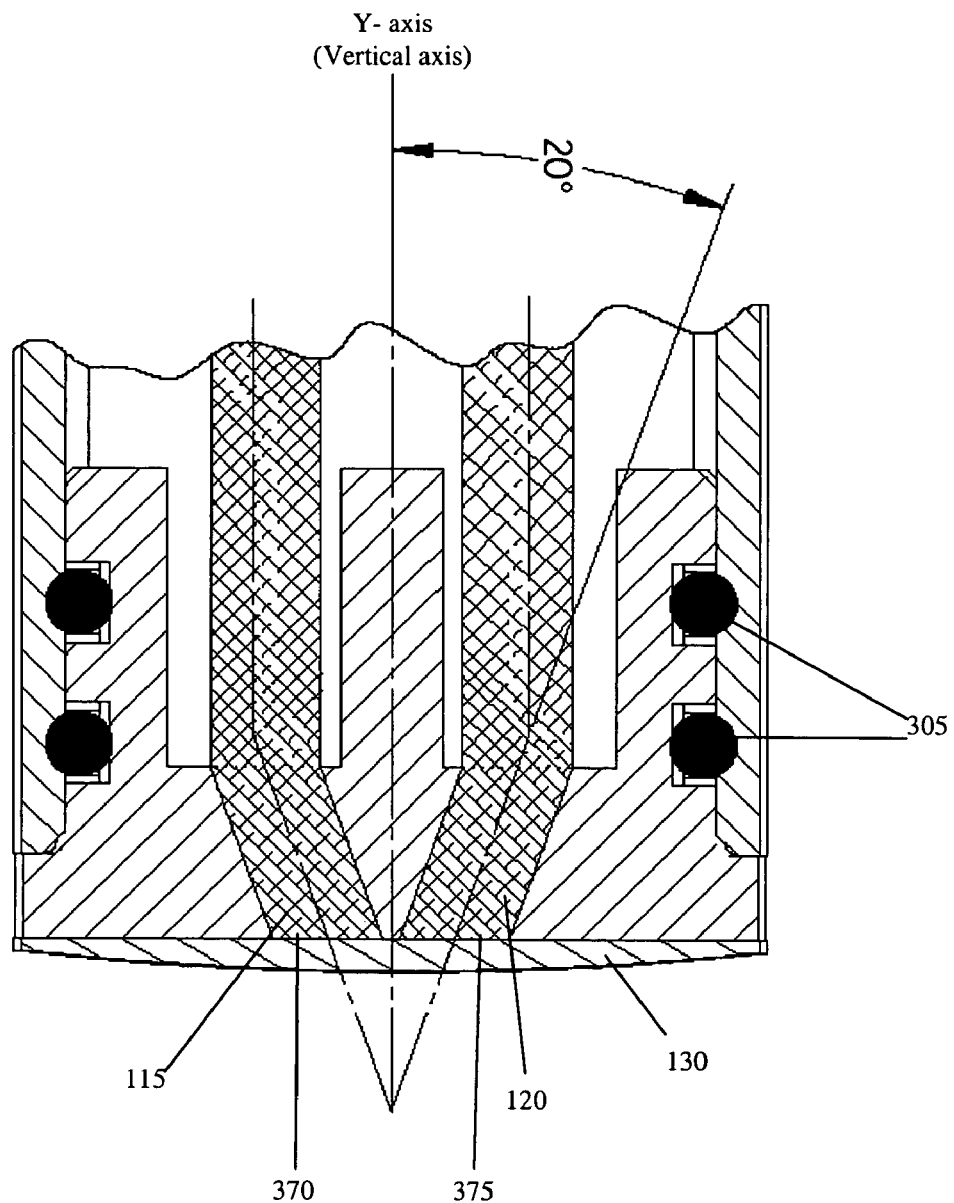
FIG. 4 is a detail cross-sectional view of the optical end of the fluorometer.

Cap 125 provides a sealing surface to prevent water from entering the fluorometer. Cap 125 also has two orifices 370 and 375 that contain two fiberoptic cables 115 and 120. Fiberoptic cable 120 carries the excitation light from the light source to the water, while fiberoptic cable 115 carries the resulting emission light (produced by the liquid in response to the excitation light) to the detector. At the distal end of the fluorometer 50, the fiberoptic cables 115 and 120 are both set into cap 125 at an approximately 20° angle with respect to a vertical axis of the cap, as shown in FIG. 4. As further shown in this figure, these settings result in about a 40° angle between the two fiberoptic cables. When light leaves the beveled end of cable 120 and enters the water, the actual angle of the light is closer to 45° due to the angle of incidence and the difference in density between the fiberoptic and the water. Similarly, the emission light collected by the fiberoptic cable 115 is closer to 45°. This approximately results in an optimal 90° between the excitation and the emission. Since the two fiberoptic ends are close to each other, the measured sample is quite small, which means the angles of the fibers are not very critical in this embodiment.

As shown in FIGS. 1 and 3, an optically clear coating 130 is applied to cap 125 and the ends of orifices 370 and 375 and fiberoptic cables 115 and 120. This optical coating 130 provides a seal around the fiberoptic cables 115 and 120 and the cap 125 and provides protection for the fiberoptic cable ends. This coating 130 (typically an epoxy) gives a smooth finish that is easily wiped clean. If ever abraded, the epoxy could be polished to once again give an optically clear finish.

Cap 125 is inserted into the tube housing, and the o-rings 305 provide sealing about the cap to prevent water from entering the fluorometer. The fiberoptic cables 115 and 120 travel through the orifice 370 and 375 of the cap 125. As shown in FIG. 3, the cables 115 and 120 travel through the chambers 370 and 375 initially at the 20° angle with respect to the vertical axis and then in parallel to this axis. The fiberoptic cables 115 and 120 then each pass through the optical chassis 365. The optional excitation filter 330 is placed between the end of the fiberoptic cable 120 and the light emitting diode (LED) 340 to select an optimal excitation wavelength of the light emitted from the LED. The sleeve 335 centers and retains the LED 340 so the maximum amount of light is transmitted into the fiberoptic cable 120.

The emission filter 315 is placed between the fiberoptic cable 115 and a photodiode 325. The emission filter selects the optimal emission wavelength, which is typically different from the excitation wavelength. The photodiode 325 detects the emitted light that is transmitted through the fiberoptic cable 115. Photodiode 325 is secured and centered by sleeve 320. Sleeve 320 may also provide electrical isolation between the case of the photodiode 325 (if the case is metal) and optical chassis 365 (if the chassis is constructed from metal).

FIGS. 2 and 3 also show that LED 340 and photodiode 325 are connected to the PCB 350. In order to prevent electrical noise from entering the pre-amplifier section of the PCB 350, the metal shield 355 covering the pre-amplifier circuitry is attached to the PCB 350 and grounded. The electrical cable 110 is soldered to PCB 350. Finally, the top of the instrument is sealed using potting material 300, though a cap similar to cap 125 could be used with a water tight connector.

Figure 5:
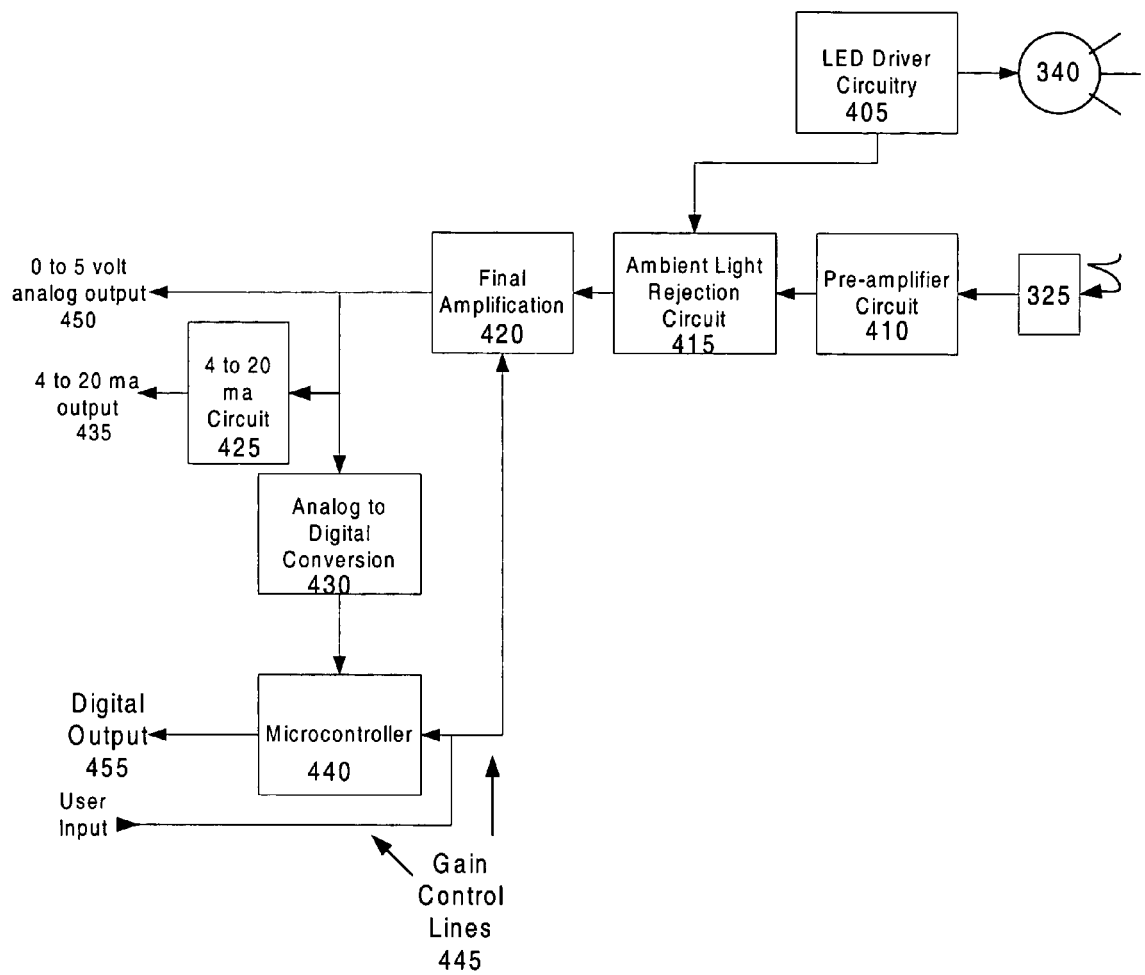
FIG. 5 is a block diagram of the electronics in the fluorometer.

FIG. 5 is a block diagram of the circuitry internal to the fluorometer and contained on PCB 350. Power provided to the fluorometer is conditioned and converted by power circuitry to provide the necessary voltages for the fluorometer circuitry. LED circuitry 405 controls the LED 340, flashing it alternately ON then OFF. When the LED circuitry 405 turns ON LED 340, excitation light from LED 340 is first filtered by filter 330 and then directed towards the water passing by the distal end of the fluorometer 50 that is inserted into the plumbing. When LED 340 is ON, the fluorescence of the water stream will produce an emission light that combines with the ambient light. When LED 340 is OFF, only ambient light will be present.

The ambient light and/or emission light produced by the excitation is picked up by fiber optic cable 115, which routes this light to the photodiode 325 through the emissions filter 315. The photodiode 325 generates a current, which is converted to a voltage and amplified by a pre-amplifier circuitry 410. The output of the pre-amplifier becomes the input for the ambient light rejection circuit 415.

The ambient light rejection circuitry 415 receives the same signal as LED 340 from the LED driver circuitry 405. By synchronizing to this signal, the ambient light rejection circuit 415 can determine whether it is examining excitation light plus ambient light (when LED 340 is ON) or just ambient light (when LED 340 is OFF). When the LED 340 if OFF, the ambient light rejection circuit 415 detects the amount of ambient light that is picked up by the photodiode 325. Subsequently, when the LED is ON, this rejection circuit 415 discards the detected ambient light contribution from the signal that it receives from the pre-amplifier circuit and that is based on the ambient and emission light detected by the photodiode. In other words, when the LED is ON, the rejection circuit subtracts the ambient light signal from the excitation plus ambient light signal to obtain a signal that is only dependent on the excitation light.

A variable amplifier circuit 420 that is controlled by gain control signals 445 amplifies the output of the light rejection circuitry 415. The variable amplifier circuit amplifies, for example, by a factor of 10, 100, or 1000 to give the user choices in the sensitivity and dynamic range of the fluorometer. The resulting 0 to 5 volt output 450 can be routed to cable 110 where an external controller can use it for control purposes. Alternatively, the 0–5 volt can be converted to alternative outputs. For example, it can be converted to a 4 to 20 ma signal by a voltage-to-current converter circuit 425. Another alternative is to convert the 0 to 5 volt output 450 to a digital signal with an Analog to Digital converter 430. This digital output can then be read by a microcontroller 440, processed internally, and reported as a serial data signal 455 to a computer through cable 110. When microcontroller 440 is used, it can automatically control the gain control lines 445 to the final amplifier circuit 420, which gives the advantage of both excellent sensitivity and a large dynamic range. Alternatively, as shown in FIG. 5, a user can manually adjust the gain control signal on the gain control line 445 in some embodiments.

In operation, power is supplied to the fluorometer through cable 110. The output signals 450, 435, and 455 are also connected to an external controller (e.g., a computer) through cable 110. These output signals are proportional to fluorescence. Therefore, an external controller can use these output signals to drive a display to show the fluorescence of the liquid and/or to control in an automated fashion a chemical process that is monitored through the fluorescence detection.

As mentioned above, the gain control signals 445 can also connected through the cable 110 to a user or an external controller. The devices 400–430 and 440 that are illustrated in FIG. 5 are in one or more IC's that are positioned on the PCB 350. These IC's are illustrated in FIG. 2 as rectangular boxes on the PCB 350.

Figure 6:
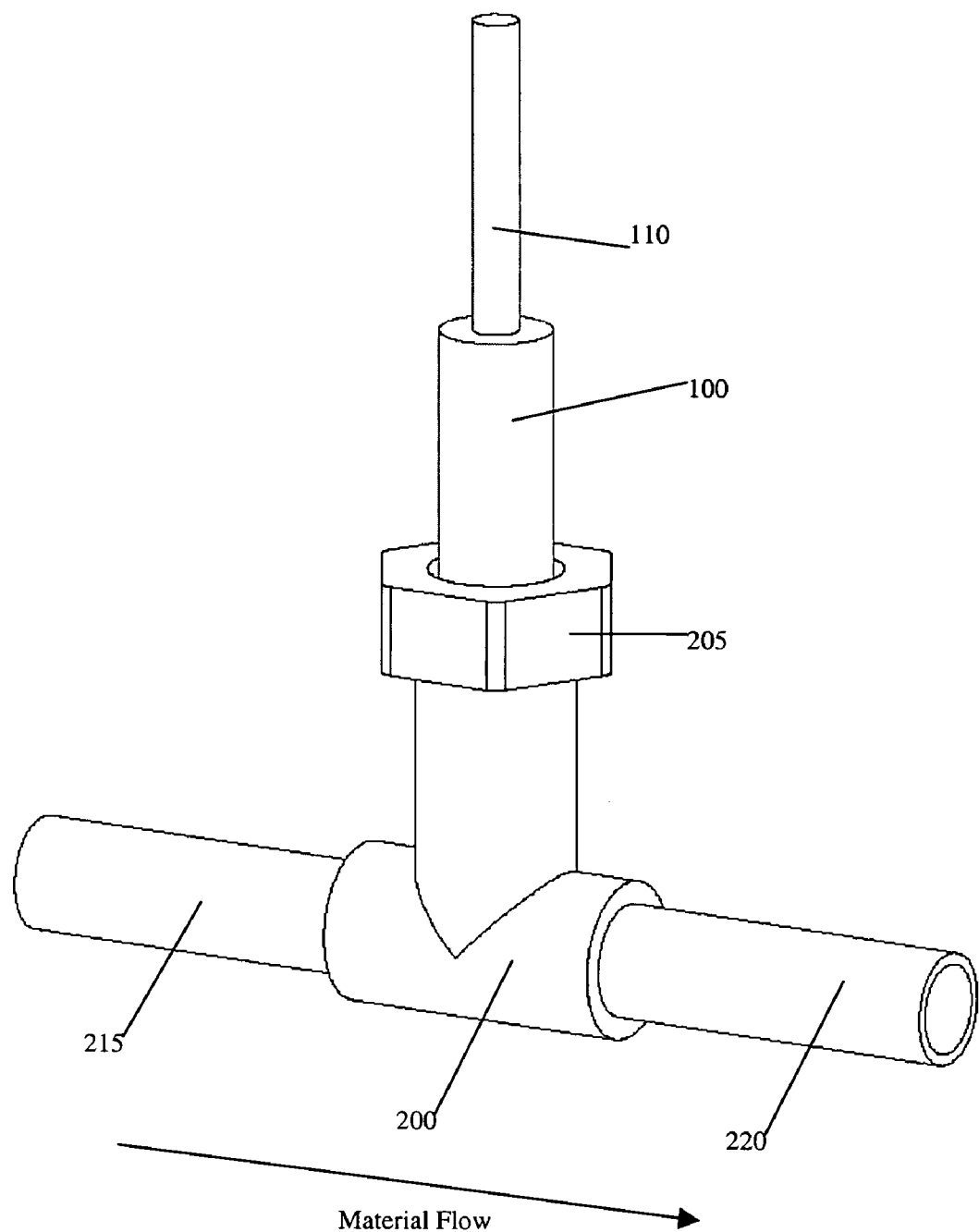
FIG. 6 is a view of the fluorometer mounted in an installation tee fitting.
Figure 7:
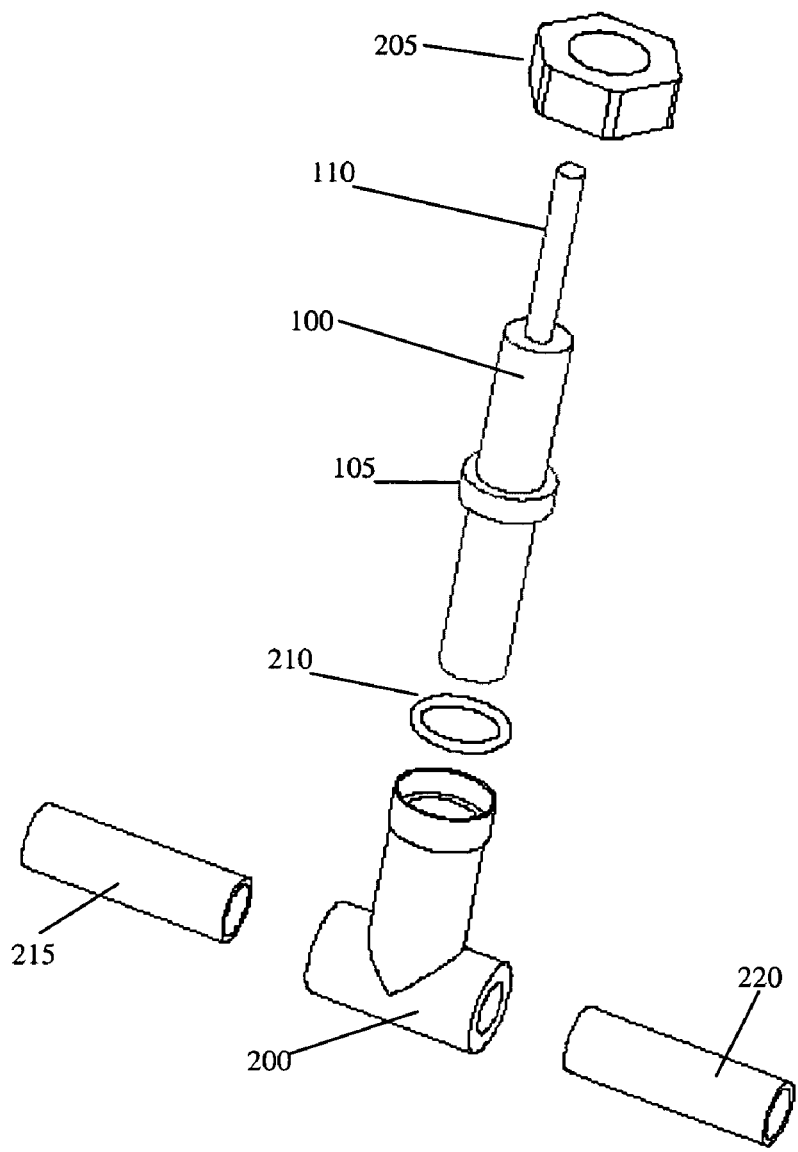
FIG. 7 is an exploded vie of the fluorometer mounted in an installation tee fitting.

In some embodiments, the fluorometer 50 is designed to fit into a standard plumbing installation tee that is often found in industrial piping. FIGS. 6 and 7 illustrate one such fitting. Specifically, FIG. 6 shows the fluorometer mounted in an installation tee 200, while FIG. 7 shows an exploded view of this fitting. FIG. 6 illustrates that the installation tee fitting 200 is inserted into a pipe system, so that a pipe 215 in this system supplies process water to the tee, while another pipe 220 in this system delivers the process water from the tee to another destination in the pipe system. As shown in FIGS. 6 and 7, the fluorometer is inserted into the installation tee fitting 200 and an o-ring 210 is placed between the collar 105 and the installation tee fitting 200 to prevent water leakage. Cap 205 is installed to squeeze collar 105 and installation tee fitting 200 together which compresses o-ring 210, forming a water tight seal and holding the fluorometer securely in place, as shown in FIG. 6.

Figure 8:
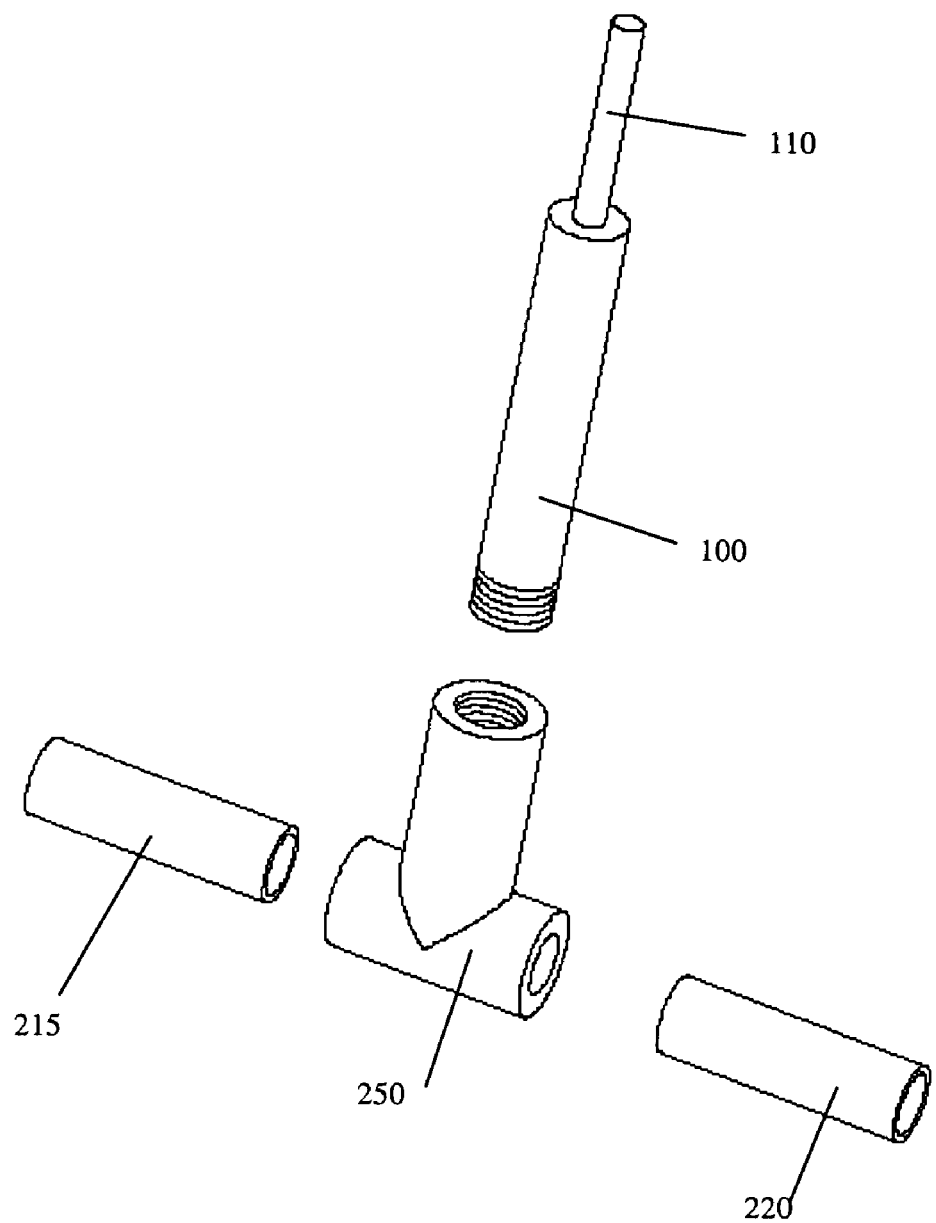
FIG. 8 is a view an alternative mounting of fluorometer in an installation tee fitting.

An alternative way for installing the fluorometer is shown in FIG. 8. In this embodiment, housing 100 is threaded at the end of the optical cap. The installation tee 250, which is used in this embodiment, has corresponding threads to accept the fluorometer. This embodiment has the advantage of using an installation tee 250 that is commonly found in plumbing systems thus making installation of the fluorometer easier for the user. Several variations of installation tee 250 exist. In one such variation, the tee 250 changes the direction of the water by 90° angle. In other words, in this tee, the angle between the pipe that brings the water into the tee and the pipe that takes the water out of the tee is 90°. The fluorometer can be placed in this tee in a chamber that is collinear with one of the pipes connected to this tee.

Figure 11:
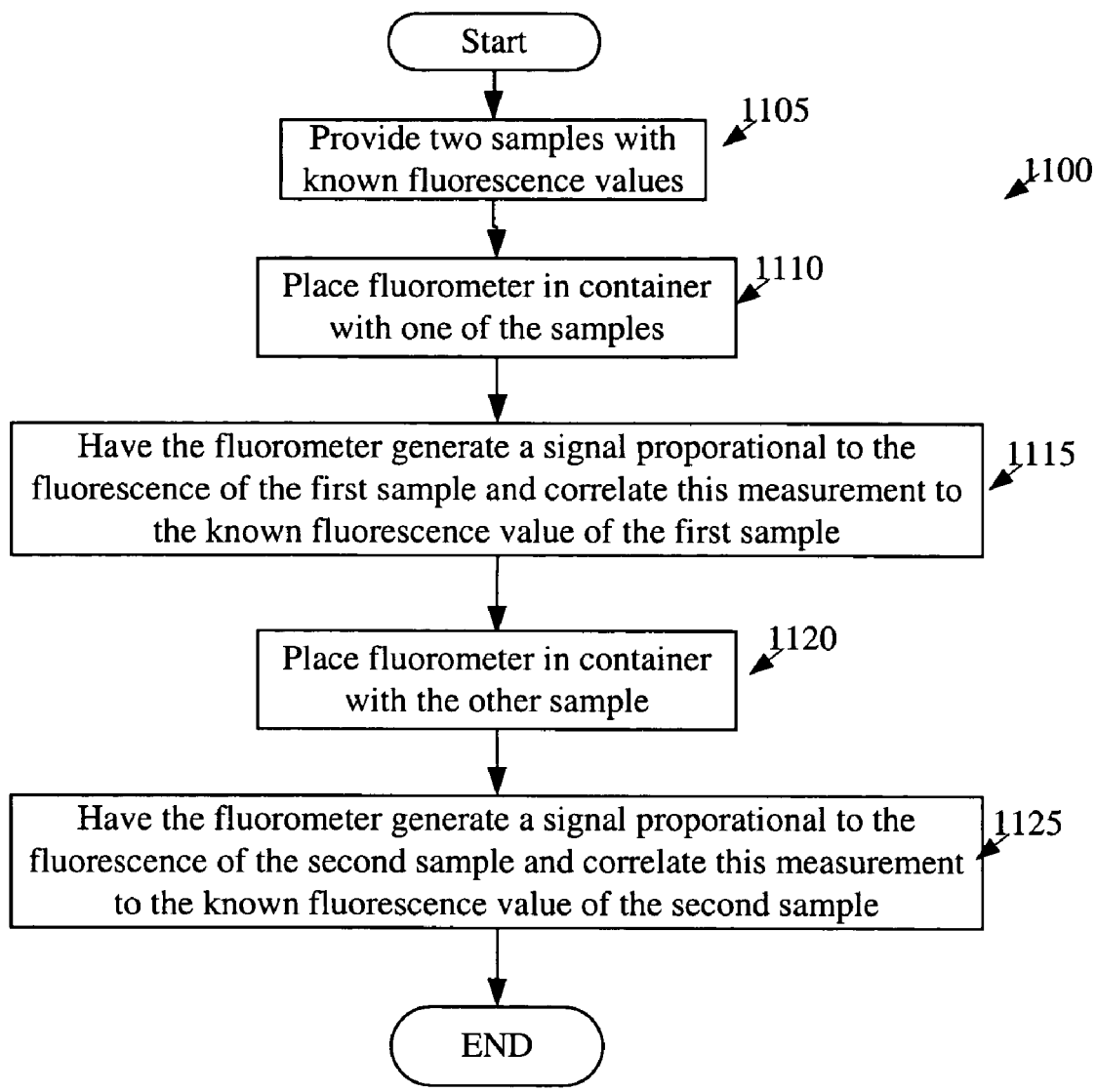
FIG. 11 illustrates a process for calibrating the fluorometer.

In some embodiments, the fluorometer is calibrated before its first operation. FIG. 11 illustrates a process 1100 for this calibration. As shown in this figure, the calibration process starts by providing (at 1105) two known samples to the fluorometer, typically a blank or zero reading plus a known dilution. Since the fluorometer includes ambient light rejection, the user need not be concerned with interference from the surrounding light. The user then places (at 1110) the fluorometer into the first blank solution in a first container and programs (at 1115) the controller to interpret the output from the fluorometer as zero. The user then places (at 1120) the fluorometer in a second container that has the second solution with known concentration, for example 100 parts per billion (ppb); the second container can be the same as the first container except that it has to be cleaned after removing the first solution before inserting the second solution. The user next programs (at 1125) the controller to interpret this output as 100. In most cases this is adequate since the fluorescent signal is linear with respect to the concentration. If the response is non-linear, many industrial controllers allow a multipoint calibration.

Once the fluorometer is calibrated, it is ready to be installed in the process stream. Water is shut off to the pipe by means of a valve. The covering cap from the installation tee fitting 200 is then removed and the fluorometer is inserted in the tee in a water-tight fit that is accomplished through a cap (such as cap 205 as shown in FIGS. 6 and 7) or through threading on the fluorometer and in the tee (as shown in FIG. 8). The process water is then returned to the pipe. If fouling occurs on the fluorometer (potentially reducing the signal), the fluorometer is removed, cap 125 is wiped clean, and the fluorometer reinserted.

The fluorometer excites the sample water with light from LED 340. The resulting emitted light is detected by photodiode 325. The circuitry on PCB 350 conditions and amplifies the signal from photodiode 325 and produces a signal proportional to fluorescence. A controller (not shown) can then use the signal from the fluorometer to turn on a pump to add more chemical when the fluorescent signal indicates the concentration is too low, and turns off the pump when the concentration reaches an upper limit.

Some embodiments have fiber optic cables 115 and 120 of the fluorometer 50 as short as possible (e.g., have these cables at 1 to 2 inches). This results in the electronics being close to the water stream. In applications where it is desirable for the electronics to be remote to the water stream (for example, if the water is extremely hot or even steam) then the fiber optic cables can be extended, such that the electronics is outside of the installation tee fitting. This allows the electronics to remain closer to ambient temperature even under extreme sample conditions.

The fluorometer 50 has several advantages. For instance, it can easily be installed in existing plumbing systems to measure a process water stream, or some other liquid stream. It also requires much less maintenance. Its maintenance is also much easier to perform as it can be easily removed and/or replaced from the plumbing system.

Figure 9:
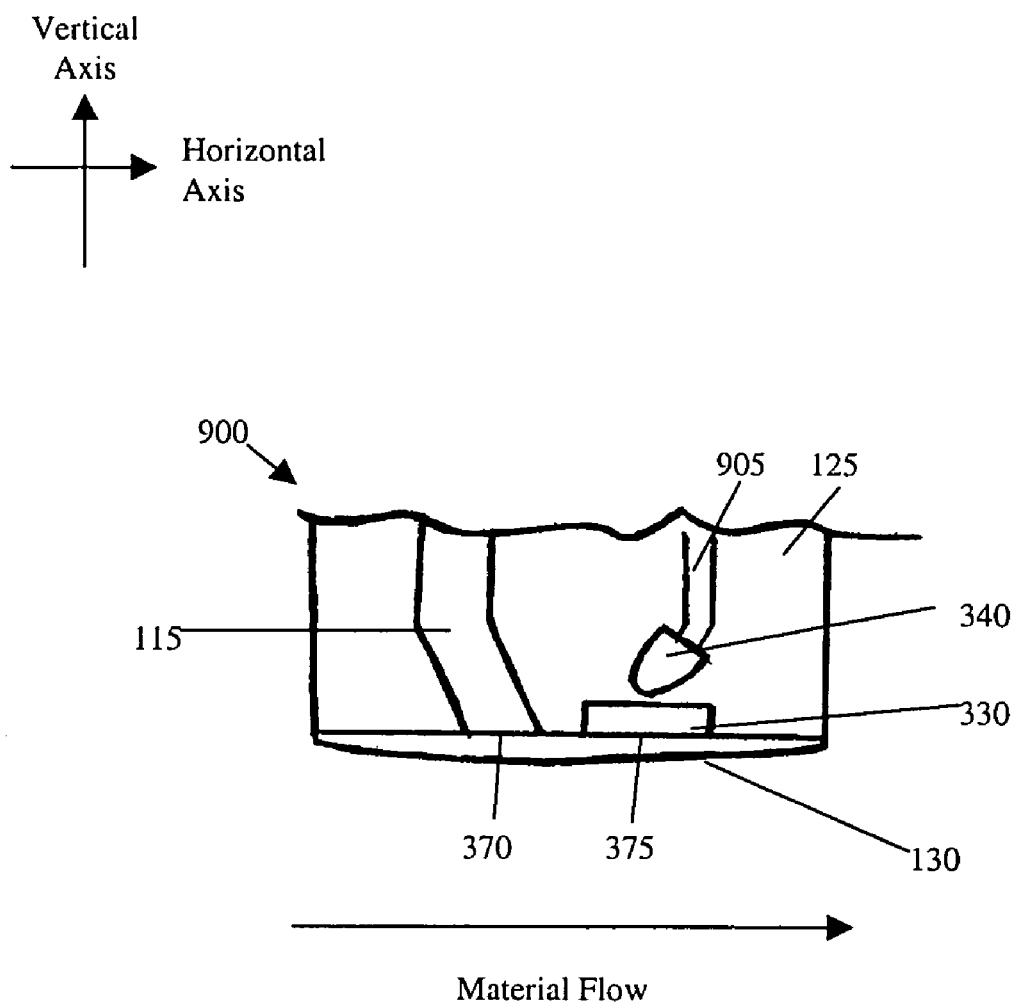
FIGS. 9 and 10 illustrate two other fluorometers of some embodiments of the invention.
Figure 10:
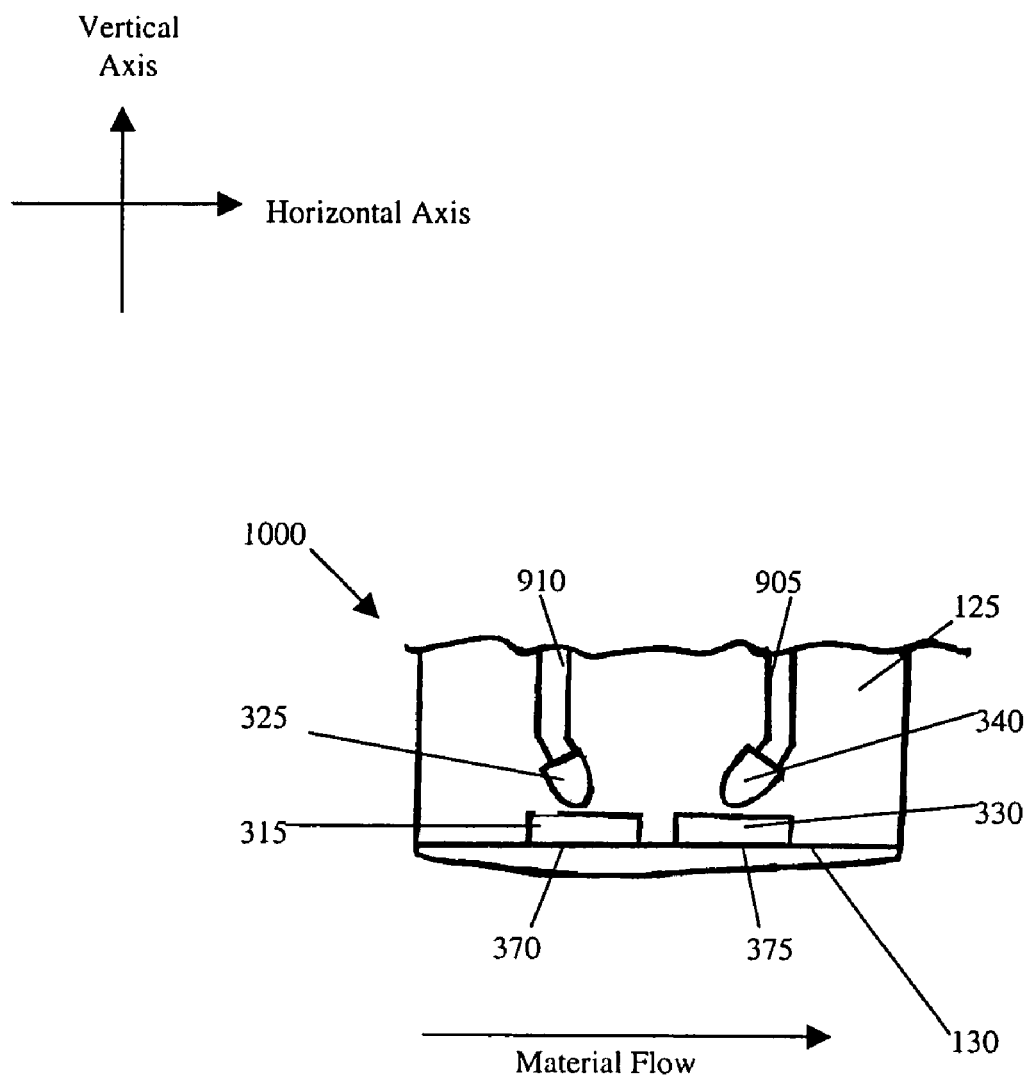

FIGS. 9 and 10 show two other fluorometers 900 and 1000 that are used in some embodiments of the invention. These figures simply show these fluorometers' distal ends (which are to be inserted in the pipe system) to illustrate the differences between these fluorometers and the fluorometer 50 that was described above. FIG. 9 illustrates a fluorometer 900 that is similar to the fluorometer 50 except for the position of its LED 340 and filter 330 and for its lack of a fiber optic cable 120. Specifically, in the fluorometer 900, the LED 340 and filter 330 are moved next to the distal end of the orifice 375 in the cap 125. The LED receives a drive signal from the LED driver circuit 405 through a conductor 905. Through the orifice 375 and filter 330, light emanates from the LED 340 onto the liquid passing by the distal end of the fluorometer that is inserted into the plumbing. As the LED 340 is moved close to the distal end of the orifice 375, there is no need for a fiber optic cable 120 to carry the light from the LED to the water. Hence, the fluorometer has no such cable.

Like the end of the fiber optic cable 120 in the fluorometer 50, the LED 340 in the fluorometer 900 is placed at an angle (e.g., 20°) with respect to the vertical axis of the the cap 125, as shown in FIG. 9. This placement of the LED results in about a 40° angle between the LED and the fiberoptic cable 115 in the fluorometer 900. When light leaves the LED and enters the water, the actual angle of the light is closer to 45° due to the angle of incidence and the difference in density between the fiberoptic and the water. Similarly, the collected emission light into fiberoptic cable 115 is closer to 45°. This approximately results in an optimal 90° angle between the excitation and the emission. Since the fiberoptic cable 115 and the LED 340 are so close to each other, the measured sample is actually quite small, which means the angles are not very critical.

FIG. 10 illustrates a fluorometer 1000 that is similar to the fluorometer 50 except for the position of its LED 340, photodiode 320, and filters 315 and 330, and for its lack of fiber optic cables 115 and 120. Like the fluorometer 900, the LED 340 and filter 330 in fluorometer 1000 are moved next to the distal end of the orifice 375 in the cap 125. However, unlike the fluorometer 900, the photodiode 325 and filter 315 are also moved next to the end of the orifice 370 in the cap 125. Through the orifice 370 and filter 315, the photodiode 325 receives light emitted off the liquid passing by the distal end of the fluorometer that is inserted into the plumbing. The photodiode 325 converts this light to a current that is passed to the pre-amplifier circuit 410 along a conductor 910. As the photodiode 325 is moved close to the distal end of the orifice 370, there is no need for a fiber optic cable 115 to carry the light from the orifice 370 to the photodiode. Hence, the fluorometer 1000 has no such cable.

Like the end of the fiber optic cable 115 of fluorometer 50, the photodiode 325 of fluorometer 1000 is placed at an angle (e.g., 20°) with respect to the cap 125, as shown in FIG. 10. Also, in some embodiment, the photodiode 325 of fluorometer 1000 of FIG. 10 has a lens to provide a narrow acceptance angle for light, in order to achieve an angle for receiving light close to the desired 20° angle. This lens along with the placement of the photodiode results in about a 40° between the LED 340 and the photodiode 325. When light leaves the LED and enters the water, the actual angle of the light is closer to 45° due to the angle of incidence and the difference in density between the fiberoptic and the water. Similarly, the emission light gathered by the photodiode 325 is closer to 45°. This approximately results in an optimal 90° angle between the excitation and the emission. Since the photodiode 325 and the LED 340 are so close to each other, the measured sample is actually quite small, which means the angles are not very critical.

Both of the fluorometers 900 and 1000 share the benefit of eliminating a junction between fiber 120 and filter 330, while the fluorometer 1000 also eliminates the junction between fiber 115 and filter 315. Junctions such as these typically result in loss of light and therefore less sensitivity to fluorescence. However, placing components at the face of the instrument increases the instrument diameter, or requires smaller sized LED 340, photodiode 325, and/or filters 330 and 315, which in turn reduces the instrument's ability to generate excitation light and capture emission light.

While the invention has been described with reference to numerous specific details, one of ordinary skill in the art will recognize that the invention can be embodied in other specific forms without departing from the spirit of the invention. For instance, in the embodiments described above, the orifices 370 and 375 are placed on the same side of the distal end of the fluorometers. However, in other embodiments, these orifices can be placed on different sides of the distal end of a fluorometer. Alternatively, these orifices can be placed on different locations of a curved surface of the distal end of a fluorometer (e.g., can be placed at opposing locations on a cylindrical or semi-spherical surface of the distal end). Yet other embodiments might only have one orifice at the distal end of the fluorometer. Through this one orifice, these embodiments might project and collect light.

Several fluorometers were described above. However, one of ordinary skill will realize that some embodiments of the invention are spectrometers that use the features described above for the invention's fluorometers. For instance, some embodiments of the invention are turbidimeters that are similar to the fluorometers 50, 900, and 1000, except for their filters 315 and 330. As mentioned above, fluorometers emit light of a certain color and receive a light of a different color. Accordingly, in a fluorometer (such as fluorometer 50, 90, or 1000) the filter 315 is different than the filter 330 (i.e., the filter 315 allows light of a different wavelength to pass through than the filter 330). On the other hand, a turbidimeter emits and receives light of the same color. Hence, the filters 315 and 330 of a turbidimeter of some embodiments would be similar (i.e., would allow the same wavelength of light to pass through). Other than having to using matching filters 315 and 330, the turbidimeters of some embodiments are identical to the fluorometers described above. Hence, the schematics illustrated in FIGS. 1–11 above are equally representative of the turbidimeters of some embodiments of the invention. Thus, one of ordinary skill in the art will understand that the invention is not to be limited by the foregoing illustrative details, but rather is to be defined by the appended claims.

What is claimed is:

1. A fluorometer for measuring fluorescence of a non-solid material flowing through a system of pipes, the fluorometer comprising:
    a) a housing having a distal end and having a shape adapted to insert into the system of pipes;
    b) a light source for passing light through the distal end towards the non-solid material, wherein the light source is a light emitting diode;
    c) a light detection circuit for receiving through the distal end light emitted from the non-solid material; and
    d) wherein the fluorometer has threads for fastening the fluorometer to an adjoining member, wherein the adjoining member has corresponding threads.

2. The fluorometer of claim 1, wherein the distal end has a first orifice optically coupled to the light source, and a second orifice optically coupled to the light detection circuit.

3. The fluorometer of claim 2 further comprising first and second light-passing conduits respectively connected to the first and second orifices, wherein the first conduit optically couples to the light source, and the second conduit optically couples to the light detection circuit.

4. The fluorometer of claim 3, wherein the light-passing conduits are fiber optic cables.

5. The fluorometer of claim 3, further comprising:
 a) an excitation filter between the light source and the first orifice, said emission filter for filtering light outside of a first wavelength band; and
 b) an emission filter between the second orifice and the light detection circuit, said emission filter for filtering light outside of a second wavelength band.

6. The fluorometer of claim 5, further comprising a chassis that aligns the light source, excitation filter, and the first light-passing conduit, and aligns the light detection circuit emission filter, and the second light-passing conduit.

7. The fluorometer of claim 2 further comprising at least one light-passing conduit connected to one of the orifices.

8. The fluorometer of claim 7, wherein the conduit optically couples the first orifice to the light source.

9. The fluorometer of claim 8, wherein the light detection circuit is positioned within the second orifice, wherein the second orifice is a chamber at the distal end, the second orifice having a distal end that faces outside of the fluorometer, wherein the distal end of the orifice is covered by a seal that allows light from the light source out of the fluorometer through the first orifice and light from the material into the fluorometer through the second orifice.

10. The fluorometer of claim 7, wherein the conduit optically couples the second orifice to the light detection circuit.

11. The fluorometer of claim 10, wherein the light source is positioned within the first orifice, wherein the first orifice is a chamber at the distal end, the first orifice having a distal end that faces outside of the fluorometer, wherein the distal end of the orifice is covered by a seal that allows light from the light source out of the fluorometer through the first orifice and light from the material into the fluorometer through the second orifice.

12. The fluorometer of claim 2, wherein the adjoining member has a passageway that allows non-solid material to flow across the distal end of the fluorometer.

13. An apparatus for measuring fluorescence of a non-solid material that flows through two pipes, the apparatus comprising:
 a) an adjoining member for connecting the first and second pipes, the adjoining member having a passageway that allows the non-solid material to flow from the first pipe to the second pipe, and the adjoining member further having a chamber that on a first end is open and at a second end terminates on the passageway;
 b) a fluorometer for inserting into the chamber to measure the fluorescence of the non-solid material, wherein the fluorometer comprises a light emitting diode; and
 c) wherein the fluorometer and the adjoining member have corresponding threads for fastening the fluorometer and the adjoining member together.

14. The apparatus of claim 13, wherein the fluorometer further comprises:
 a) a housing having a distal end and having a shape adapted to insert into the system of pipes; and
 b) a light detection circuit for receiving through the distal end light emitted from the non-solid material,
 wherein the light emitting diode passes light through the distal end towards the non-solid material.

15. The apparatus of claim 14 further comprising a fastening member for fastening the adjoining member and the fluorometer.

16. An apparatus for measuring fluorescence of a non-solid material, the apparatus comprising:
 a) two pipes through which the non-solid material flows;
 b) an adjoining member that connects the two pipes, the adjoining member having a passageway that allows non-solid material to flow from one pipe to the other, and the adjoining member further having a chamber that on a first end is open and at a second end terminates on the passageway; and
 c) a fluorometer inserted into the chamber for measuring the fluorescence of the non-solid material, wherein the fluorometer and the adjoining member have corresponding threads for fastening the fluorometer and the adjoining member together.

17. A fluorometer for measuring fluorescence of a non-solid material, the fluorometer comprising:
 a) first and second orifices on a side of the fluorometer that is to be placed next to the non-solid material;
 b) a light source for passing light through the first orifice and onto the non-solid material, wherein the light source is a light emitting diode;
 c) a light detection circuit for receiving through the second orifice light emitted from the non-solid material; and
 d) a tube shaped housing shaped to insert into a system of pipes, wherein the tube shaped housing contains the light source, the light detection circuit, and a printed circuit board, wherein the printed circuit board contains electronic circuitry of the fluorometer.

18. The fluorometer of claim 17 further comprising first and second light-passing conduits respectively connected to the first and second orifices, wherein the first conduit couples to the light source, and the second conduit couples to the light detection circuit.

19. A method of measuring fluorescence of a non-solid material flowing through a system of pipes, the method comprising:
 a) inserting the fluorometer into an adjoining member of the pipe system that connects two pipes in the system;
 b) directing light from a light emitting diode in the fluorometer onto the non-solid material flowing between the two pipes;
 c) collecting into the fluorometer the light emitted off the non-solid material;
 d) based on the collected light, generating an electrical signal that is proportional to the fluorescence of the non-solid material; and
 e) wherein the fluorometer and the adjoining member have corresponding threads for fastening the fluorometer and the adjoining member together.

20. The method of claim 19 further comprising fastening the fluorometer and adjoining member by using a material-tight seal.

21. The method of claim 19 further comprising calibrating the fluorometer before inserting the fluorometer into the pipe system, wherein calibrating the fluorometer comprises:
 placing the fluorometer in a first sample having a known first fluorescence value, performing said directing, collecting, and generating operations to compute a first electrical signal, and correlating the first electrical signal to the first fluorescence value;
 placing the fluorometer in a second sample having a known second fluorescence value, performing said directing, collecting, and generating operations to compute a second electrical signal, and correlating the second electrical signal to the second fluorescence value.

22. A spectrometer for measuring light from a non-solid material flowing through a system of pipes, the spectrometer comprising:
　　a) a tube shaped housing having a distal end and having a shape adapted to insert into the system of pipes;
　　b) a light source for passing light through the distal end towards the non-solid material, wherein the light source is a light emitting diode;
　　c) a light detection circuit for receiving, through the distal end, light from the non-solid material; and
　　d) wherein the tube shaped housing contains the light source, the light detection circuit, and a printed circuit board, wherein the printed circuit board contains electronic circuitry of the spectrometer.

23. The spectrometer of claim 22, wherein the distal end has a first orifice optically coupled to the light source, and a second orifice optically coupled to the light detection circuit.

24. The spectrometer of claim 23 further comprising first and second light-passing conduits respectively connected to the first and second orifices, wherein the first conduit optically couples to the light source, and the second conduit optically couples to the light detection circuit.

25. The spectrometer of claim 23 further comprising at least one light-passing conduit connected to one of the orifices.

26. The spectrometer of claim 25, wherein the conduit optically couples the first orifice to the light source.

27. The spectrometer of claim 26, wherein the light detection circuit is positioned within the second orifice, wherein the second orifice is a chamber at the distal end, the second orifice having a distal end that faces outside of the spectrometer, wherein the distal end of the orifice is covered by a seal that allows light from the light source out of the spectrometer through the first orifice and light from the material into the spectrometer through the second orifice.

28. The spectrometer of claim 25, wherein the conduit optically couples the second orifice to the light detection circuit.

29. The spectrometer of claim 28, wherein the light source is positioned within the first orifice, wherein the first orifice is a chamber at the distal end, the first orifice having a distal end that faces outside of the spectrometer, wherein the distal end of the orifice is covered by a seal that allows light from the light source out of the spectrometer through the first orifice and light from the material into the spectrometer through the second orifice.

30. The spectrometer of claim 22, wherein the spectrometer is a turbidimeter.

31. The spectrometer of claim 22, wherein the spectrometer is a fluorometer.

32. An apparatus for measuring light from a non-solid material that flows through two pipes, the apparatus comprising:
　　a) an adjoining member for connecting the first and second pipes, the adjoining member having a passageway that allows the non-solid material to flow from the first pipe to the second pipe, and the adjoining member further having a chamber that on a first end is open and at a second end terminates on the passageway;
　　b) a spectrometer for inserting into the chamber to emit light towards the non-solid material and measure light from the non-solid material, wherein the spectrometer comprises a light emitting diode and
　　c) wherein the spectrometer and the adjoining member have corresponding threads for fastening the spectrometer and the adjoining member together.

33. The apparatus of claim 32, wherein the spectrometer further comprises:
　　a) a housing having a distal end and having a shape adapted to insert into the system of pipes; and
　　b) a light detection circuit for receiving through the distal end light from the non-solid material,
　　wherein the light emitting diode passes light through the distal end towards the non-solid material.

34. The apparatus of claim 33 further comprising a fastening member for fastening the adjoining member and the spectrometer.

35. A fluorometer for measuring fluorescence of a non-solid material flowing through a system of pipes, the fluorometer comprising:
　　a) a tube shaped housing having a distal end and having a shape adapted to insert into the system of pipes;
　　b) a light source for passing light through the distal end towards the non-solid material;
　　c) a light detection circuit for receiving through the distal end light emitted from the non-solid material, and
　　wherein the tube shaped housing contains the light source, the light detection circuitry, and a printed circuit board, wherein the printed circuit board contains electronic circuitry of the fluorometer.

36. The fluorometer of claim 35, wherein the tube shaped housing contains substantially all of the fluorometer.

\* \* \* \* \*

UNITED STATES PATENT AND TRADEMARK OFFICE
CERTIFICATE OF CORRECTION

PATENT NO. : 7,099,012 B1
APPLICATION NO. : 10/687520
DATED : August 29, 2006
INVENTOR(S) : James Crawford et al.

Page 1 of 1

It is certified that error appears in the above-identified patent and that said Letters Patent is hereby corrected as shown below:

<u>Column 12</u>
Line 15 Claim 32 reads "… comprises a light emitting diode and …"
Should read (correction of a semicolon) --…comprises light emitting diode; and …--

Signed and Sealed this

Thirtieth Day of January, 2007

JON W. DUDAS
*Director of the United States Patent and Trademark Office*